United States Patent [19]
Kato et al.

[11] Patent Number: 6,059,947
[45] Date of Patent: May 9, 2000

[54] GAS SENSOR

[75] Inventors: Nobuhide Kato, Ama-gun; Yasuhiko Hamada, Nagoya, both of Japan

[73] Assignee: NGK Insulators, Ltd., Japan

[21] Appl. No.: 09/098,597

[22] Filed: Jun. 17, 1998

[30] Foreign Application Priority Data

Jul. 14, 1997 [JP] Japan .................................. 9-188578

[51] Int. Cl.⁷ .................................................. G01N 27/26
[52] U.S. Cl. ........................ 204/425; 204/401; 204/408; 204/426
[58] Field of Search .................................. 204/425, 426, 204/427, 408, 401; 205/781, 784.5

[56] References Cited

U.S. PATENT DOCUMENTS

| | | |
|---|---|---|
| 4,824,549 | 4/1989 | Hamada et al. . |
| 4,905,652 | 3/1990 | Nakajima et al. . |
| 4,981,125 | 1/1991 | Kato et al. . |

FOREIGN PATENT DOCUMENTS

| | | |
|---|---|---|
| 0 678 740 A1 | 10/1995 | European Pat. Off. . |
| 0 769 693 A1 | 4/1997 | European Pat. Off. . |
| 63-38154 | 2/1988 | Japan . |
| 64-39545 | 2/1989 | Japan . |
| 1-277751 | 11/1989 | Japan . |
| 2-1543 | 1/1990 | Japan . |

*Primary Examiner*—Robert J. Warden, Sr.
*Assistant Examiner*—Kaj K. Olsen
*Attorney, Agent, or Firm*—Parkhurst & Wendel, L.L.P.

[57] ABSTRACT

A gas sensor comprises a main pumping cell for pumping-processing oxygen contained in a first chamber, a feedback control system for comparing a partial pressure of oxygen in the first chamber with a first reference value to control the main pumping cell so that the partial pressure of oxygen has a predetermined value at which NO is not decomposable, an auxiliary pumping cell for pumping-processing oxygen in the second chamber, and a measuring pumping cell for pumping-processing oxygen produced by decomposition of NOx. The gas sensor further comprises a correcting control system for correcting and controlling the feedback control system on the basis of a difference between a second reference value and a value of a pumping current flowing through the auxiliary pumping cell to give a constant oxygen concentration in the second chamber, and a self-diagnosis unit for comparing the value of the pumping current with a prescribed range and judging whether or not any trouble occurs, on the basis of an obtained result of comparison. Accordingly, it is possible to provide the gas sensor having a self-diagnosis function capable of quickly and reliably detecting whether or not any trouble occurs.

10 Claims, 11 Drawing Sheets

GAS SENSOR

BACKGROUND OF THE INVENTION

1. Field of the Invention

The present invention relates to a gas sensor for measuring oxides such as NO, $N_2$, $SO_2$, $CO_2$, and $H_2O$ contained in, for example, atmospheric air and exhaust gas discharged from vehicles or automobiles, and inflammable gases such as CO and CnHm.

2. Description of the Related Art

Various measuring systems and apparatuses have been hitherto suggested in order to know the concentration of a desired gas component in a measurement gas.

For example, those known as the method for measuring NOx in a measurement gas such as combustion gas include a technique in which the NOx-reducing ability of Rh is utilized while using a sensor comprising a Pt electrode and an Rh electrode formed on an oxygen ion-conductive solid electrolyte such as zirconia to measure an electromotive force generated between the both electrodes.

The sensor as described above suffers the following problem. That is, the electromotive force is greatly changed depending on the change in concentration of oxygen contained in a combustion gas as a measurement gas. Moreover, the change in electromotive force is small with reason, the conventional sensor tends to suffer influence of noise. Further, in order to bring out the NOx-reducing ability, it is indispensable to use a reducing gas such as CO. For this reason, the amount of produced CO is generally smaller than the amount of produced NOx under a lean fuel combustion condition in which a large amount of NOx is produced. Therefore, the conventional sensor has a drawback in that it is impossible to perform measurement for a combustion gas produced under such a combustion condition.

A system has been disclosed, for example, in Japanese Laid-Open Patent Publication Nos. 63-38154 and 64-39545, in which a pair of electrochemical pumping cell and sensor cell comprising Pt electrode and an oxygen ion-conductive solid electrolyte are combined with another pair of electrochemical pumping cell and sensor cell comprising Rh electrode and an oxygen ion-conductive solid electrolyte to measure NOx in accordance with a difference between respective pumping current values.

Further, for example, Japanese Laid-Open Patent Publication Nos. 1-277751 and 2-1543 disclose the following method. That is, two pairs of electrochemical pumping cells and sensor cells are prepared. The limiting pumping current is measured at a partial pressure of oxygen at which NOx is not reduced, by using a sensor comprising one of the pairs of pumping cells and sensor cells, while the limiting pumping current is measured at a partial pressure of oxygen at which NOx is reduced, by using a sensor comprising the other pair of pumping cell and sensor cell so that the difference between the limiting pumping currents is determined. Besides, the difference in limiting current is measured by using a sensor comprising a pair of pumping cell and sensor cell, while switching the partial pressure of oxygen in a measurement gas between a partial pressure of oxygen at which NOx is reduced and a partial pressure of oxygen at which NOx is not reduced.

SUMMARY OF THE INVENTION

The present invention relates to the gas sensor as described above, an object of which is to provide a gas sensor which has a self-diagnosis function capable of quickly and reliably detecting whether or not the gas sensor has any trouble.

According to the present invention, there is provided a gas sensor comprising a main pumping means for pumping-processing oxygen contained in a measurement gas introduced from an external space into a processing space formed and comparted by solid electrolytes contacting with the external space; a main pumping control means for comparing a partial pressure of oxygen in the processing space with a first reference value to control the main pumping means so that the partial pressure of oxygen has a predetermined value at which a predetermined gas component as a measurement objective is not decomposable; and an electric signal-generating conversion means for making conversion into an electric signal corresponding to an amount of oxygen contained in the measurement gas after being pumping-processed by the main pumping means; wherein a measurement gas component contained in the measurement gas is measured on the basis of the electric signal supplied from the electric signal-generating conversion means; the gas sensor further comprising an oxygen concentration-detecting means for detecting a concentration of oxygen contained in the measurement gas after being pumping-processed by the main pumping means; a correcting control means for correcting and controlling the main pumping control means on the basis of a difference between a detected value supplied from the oxygen concentration-detecting means and a second reference value to give a constant concentration of oxygen contained in the measurement gas after being pumping-processed by the main pumping means; and a self-diagnosis means for comparing the detected value supplied from the oxygen concentration-detecting means with a prescribed range to decide whether or not any trouble occurs, on the basis of a result of the comparison.

According to the present invention, at first, the oxygen, which is contained in the measurement gas introduced from the external space, is pumping-processed by the main pumping means, and the oxygen is adjusted to have a predetermined concentration. The measurement gas, which has been adjusted for the oxygen concentration by the main pumping means, is introduced into the electric signal-generating conversion means in the next step. The electric signal-generating conversion means decomposes the measurement gas component contained in the introduced measurement gas by means of catalytic action and/or electrolysis, to make conversion into the electric signal corresponding to the amount of oxygen produced by the decomposition. The measurement gas component contained in the measurement gas is measured on the basis of the electric signal supplied from the electric signal-generating conversion means.

The detecting operation described above is performed while heating at least the main pumping means and the electric signal-generating conversion means to predetermined temperatures by the aid of a heater. Therefore, the amount of the predetermined component is detected highly accurately by using the electric signal-generating conversion means.

The predetermined gas component includes, for example, NO, and the measurement gas component includes, for example, NOx.

When the electric signal-generating conversion means comprises a measuring pumping means, the measurement gas, which has been adjusted for the oxygen concentration by the main pumping means, is introduced into the measuring pumping means.

The measuring pumping means decomposes the measurement gas component after being pumping-processed by the main pumping means, by means of catalytic action and/or electrolysis, and it pumping-processes oxygen produced by the decomposition. The predetermined gas component corresponding to an amount of oxygen is measured on the basis of a pumping current generated in the measuring pumping means in accordance with the amount of oxygen pumping-processed by the measuring pumping means.

In another embodiment, the electric signal-generating conversion means comprises a concentration-detecting means. In this case, the measurement gas, which has been adjusted for the oxygen concentration by the main pumping means, is introduced into the concentration-detecting means in the next step. An electromotive force of an oxygen concentration cell is generated in the concentration-detecting means, which corresponds to a difference between an amount of oxygen contained in a reference gas and an amount of oxygen produced by decomposition of the predetermined gas component contained in the measurement gas. The predetermined gas component corresponding to the amount of oxygen is measured on the basis of the electromotive force.

During the period in which the measurement operation is performed for the predetermined gas component, the concentration of oxygen contained in the measurement gas after being pumping-processed by the main pumping means is detected by the aid of the oxygen concentration-detecting means. Further, the main pumping control means is corrected and controlled on the basis of the difference between the detected value supplied from the oxygen concentration-detecting means and the second reference value by the aid of the correcting control means. Thus, the concentration of oxygen contained in the measurement gas after being pumping-processed by the main pumping means is made constant.

Accordingly, it is possible to avoid the deterioration of accuracy which would be otherwise caused by leakage and invasion of oxygen brought about by large change in oxygen concentration in the measurement gas. Further, it is possible to avoid the deterioration of accuracy which would be otherwise involved in slight decomposition of $H_2O$ brought about by increase in concentration of $H_2O$ in the measurement gas. Moreover, it is possible to avoid the occurrence of the two types of deterioration of accuracy which would be otherwise caused by temperature change as well as the occurrence of the two types of deterioration of accuracy which would be otherwise caused by deterioration of the main pumping means.

Further, in the gas sensor according to the present invention, the self-diagnosis means is used to compare the detected value supplied from the oxygen concentration-detecting means with the prescribed range so that it is decided whether or not any trouble occurs, on the basis of the result of comparison.

In general, the main pumping means of the gas sensor is operated such that the oxygen contained in the measurement gas introduced from the external space into the processing space is pumping-processed in accordance with the control operation effected by the main pumping control means so that the value of the partial pressure of oxygen in the processing space is the predetermined value at which the measurement gas component as the measurement objective is not decomposable.

Therefore, if the concentration of oxygen contained in the measurement gas after being pumping-processed by the main pumping means cannot be made constant although the main pumping control means is corrected and controlled by the aid of the correcting control means, namely if the detected value supplied from the oxygen concentration-detecting means does not arrived at the prescribed range, then the gas sensor is out of order due to any cause (for example, disconnection of the control system or the heater or malfunction of the electrode). In the present invention, it is decided whether or not any trouble occurs in the gas sensor, by utilizing the foregoing principle. Accordingly, the present invention makes it possible to promptly and reliably detect whether or not the gas sensor is in a failure state at present. Therefore, it is possible to make quick response to maintain and manage the gas sensor. The malfunction of the electrode is exemplified by exhaustion and peeling-off of the electrode due to thermal damage, and decrease in catalytic activity of the electrode due to, for example, poisoning and clogging.

It is preferable for the gas sensor according to the present invention described above that the oxygen concentration-detecting means comprises an auxiliary pumping means for pumping-processing oxygen contained in the measurement gas after being pumping-processed by the main pumping means, and a value of a pumping current flowing through the auxiliary pumping means is used as the detected value of oxygen concentration. Alternatively, it is preferable that the oxygen concentration-detecting means comprises an oxygen partial pressure-detecting means for detecting a difference in partial pressure between oxygen contained in the measurement gas after being pumping-processed by the main pumping means and oxygen contained in a reference gas space, and a value of an electromotive force generated on the basis of the difference in partial pressure is used as the detected value of oxygen concentration.

The correcting control means may comprise a comparing means for determining a difference between the detected value supplied from the oxygen concentration-detecting means and the second reference value, and a reference value-correcting means for reflecting the difference supplied from the comparing means to the first reference value for the main pumping means.

The gas sensor according to the present invention may be constructed such that the self-diagnosis means judges that any trouble occurs, when the detected value supplied from the oxygen concentration-detecting means does not arrive at the prescribed range for a predetermined period of time.

In this embodiment, the self-diagnosis means comprises a comparing means for comparing the detected value supplied from the oxygen concentration-detecting means with the prescribed range, and a monitoring means for temporarily or periodically monitoring a comparison output supplied from the comparing means and judging that any trouble occurs, when the comparison output does not arrive at the prescribed range for a predetermined period of time.

The monitoring means may monitor the comparison output supplied from the comparing means for the predetermined period of time, upon completion of a predetermined condition. Alternatively, the monitoring means may monitor the comparison output supplied from the comparing means at intervals of a certain period of time for the predetermined period of time. Further alternatively, the monitoring means may be operated in accordance with a combination of the procedures described above.

As described above, according to the gas sensor concerning the present invention, it is possible to promptly and reliably detect whether or not the gas sensor is in a failure state at present. Therefore, it is possible to make quick response to maintain and manage the gas sensor.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Explanation will be made below with reference to FIGS. 1 to 11 for several illustrative embodiments in which the gas sensor according to the present invention is applied to gas sensors for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm.

Figure 1:
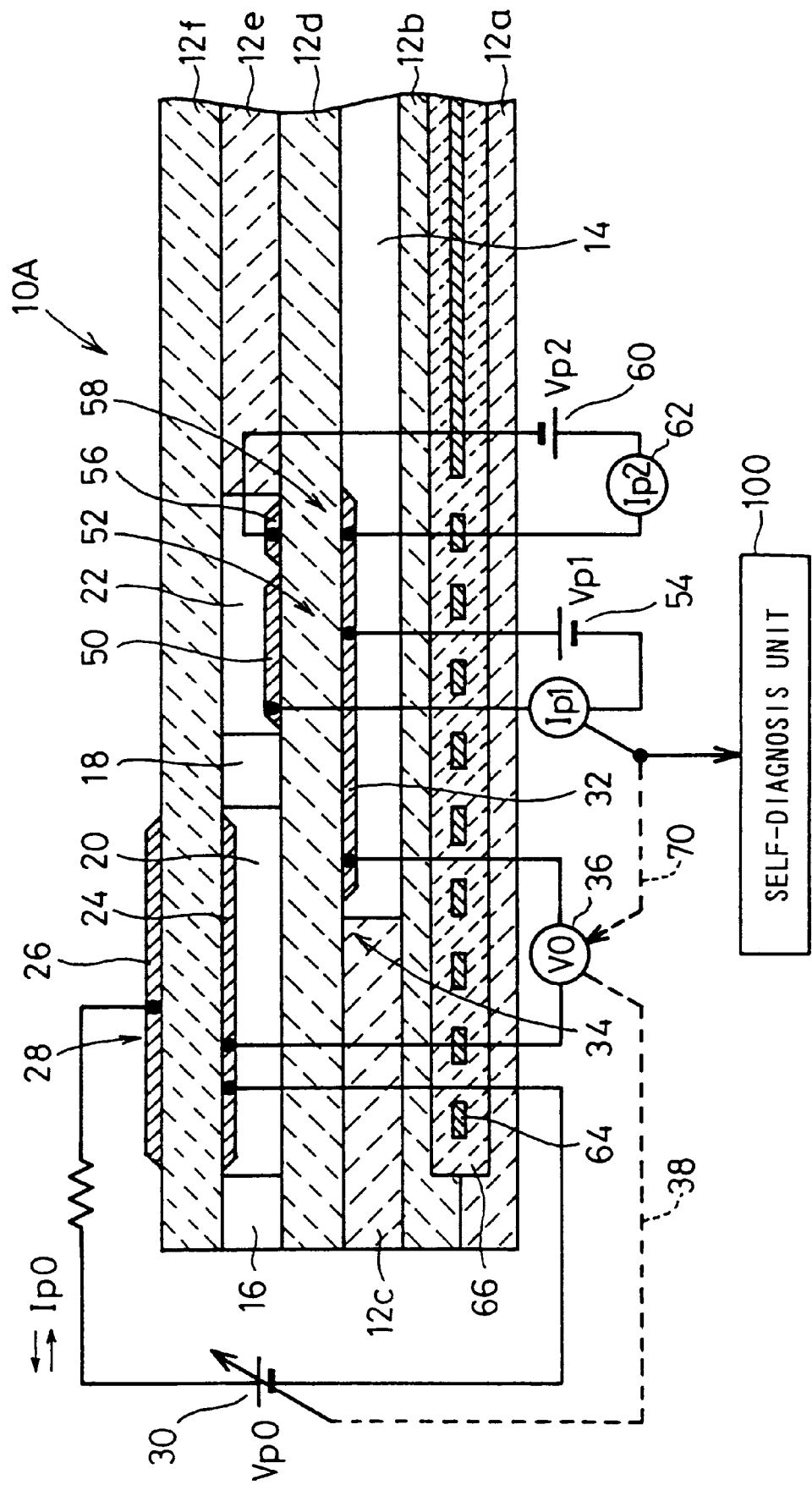
FIG. 1 shows a cross-sectional view illustrating a gas sensor according to a first embodiment.

At first, as shown in FIG. 1, a gas sensor 10A according to the first embodiment comprises, for example, six stacked solid electrolyte layers 12a to 12f composed of ceramics based on the use of oxygen ion-conductive solid electrolytes such as $ZrO_2$. First and second layers from the bottom are designated as first and second substrate layers 12a, 12b respectively. Third and fifth layers from the bottom are designated as first and second spacer layers 12c, 12e respectively. Fourth and sixth layers from the bottom are designated as first and second solid electrolyte layers 12d, 12f respectively.

Specifically, the first spacer layer 12c is stacked on the second substrate layer 12b. The first solid electrolyte layer 12d, the second spacer layer 12e, and the second solid electrolyte layer 12f are successively stacked on the first spacer layer 12c.

A space (reference gas-introducing space) 14, into which a reference gas such as atmospheric air to be used as a reference for measuring oxides is introduced, is formed between the second substrate layer 12b and the first solid electrolyte layer 12d, the space 14 being comparted by a lower surface of the first solid electrolyte layer 12d, an upper surface of the second substrate layer 12b, and side surfaces of the first spacer layer 12c.

The second spacer layer 12e is interposed between the first and second solid electrolyte layers 12d, 12f. First and second diffusion rate-determining sections 16, 18 are also interposed between the first and second solid electrolyte layers 12d, 12f.

A first chamber 20 for adjusting the partial pressure of oxygen in a measurement gas is formed and comparted by a lower surface of the second solid electrolyte layer 12f, side surfaces of the first and second diffusion rate-determining sections 16, 18, and an upper surface of the first solid electrolyte layer 12d. A second chamber 22 for finely adjusting the partial pressure of oxygen in the measurement gas and measuring oxides, for example, nitrogen oxides (NOx) in the measurement gas is formed and comparted by a lower surface of the second solid electrolyte layer 12f, a side surface of the second diffusion rate-determining section 18, a side surface of the second spacer layer 12e, and an upper surface of the first solid electrolyte layer 12d.

The external space communicates with the first chamber 20 via the first diffusion-rate determining section 16, and the first chamber 20 communicates with the second chamber 22 via the second diffusion rate-determining section 18.

The first and second diffusion-rate determining sections 16, 18 give predetermined diffusion resistances to the measurement gas to be introduced into the first and second chambers 20, 22 respectively. Each of the first and second diffusion-rate determining sections 16, 18 can be formed as a passage composed of, for example, a porous material (for example, a porous compact composed of $ZrO_2$ or the like), or a small hole having a predetermined cross-sectional area so that the measurement gas may be introduced. Alternatively, each of the first and second diffusion-rate determining sections 16, 18 may be constructed by a gap layer or a porous layer produced by printing. In this embodiment, the comparative magnitude does not matter between the respective diffusion resistances of the first and second diffusion rate-determining sections 16, 18. However, it is preferable that the diffusion resistance of the second diffusion rate-determining section 18 is larger than that of the first diffusion rate-determining section 16.

The atmosphere in the first chamber 20 is introduced into the second chamber 22 under the predetermined diffusion resistance via the second diffusion rate-determining section 18.

An inner pumping electrode 24 having a substantially rectangular planar configuration and composed of a porous cermet electrode is formed on the entire lower surface portion for forming the first chamber 20, of the lower surface of the second solid electrolyte layer 12f. An outer pumping electrode 26 is formed on a portion corresponding to the inner pumping electrode 24, of the upper surface of the second solid electrolyte layer 12f. An electrochemical pumping cell, i.e., a main pumping cell 28 is constructed by the inner pumping electrode 24, the outer pumping electrode 26, and the second solid electrolyte layer 12f interposed between the both electrodes 24, 26.

A desired control voltage (pumping voltage) Vp0 is applied between the inner pumping electrode 24 and the outer pumping electrode 26 of the main pumping cell 28 by the aid of an external variable power source 30 to allow a pumping current IpO to flow in a positive or negative direction between the outer pumping electrode 26 and the inner pumping electrode 24. Thus, the oxygen in the atmosphere in the first chamber 20 can be pumped out to the external space, or the oxygen in the external space can be pumped into the first chamber 20.

A reference electrode 32 is formed on a lower surface portion exposed to the reference gas-introducing space 14, of the lower surface of the first solid electrolyte layer 12d. An electrochemical sensor cell, i.e., a controlling oxygen partial pressure-detecting cell 34 is constructed by the inner pumping electrode 24, the reference electrode 32, the second solid electrolyte layer 12f, the second spacer layer 12e, and the first solid electrolyte layer 12d.

The controlling oxygen partial pressure-detecting cell 34 is operated as follows. That is, an electromotive force (voltage) VO is generated between the inner pumping electrode 24 and the reference electrode 32 on the basis of a difference in oxygen concentration between the atmosphere in the first chamber 20 and the reference gas (atmospheric air) in the reference gas-introducing space 14. The partial pressure of oxygen in the atmosphere in the first chamber 20 can be detected by using the electromotive force VO.

That is, the voltage VO generated between the reference electrode 32 and the inner pumping electrode 24 is an electromotive force of the oxygen concentration cell generated on the basis of the difference between the partial pressure of oxygen of the reference gas introduced into the reference gas-introducing space 14 and the partial pressure of oxygen of the measurement gas in the first chamber 20. The voltage VO has the following relationship known as the Nernst's equation.

$$VO = RT/4F \cdot \ln(P1(O_2)/P0(O_2))$$

R: gas constant;

T: absolute temperature;

F: Faraday constant;

$P1(O_2)$: partial pressure of oxygen in the first chamber 20;

$P0(O_2)$: partial pressure of oxygen in the reference gas.

Therefore, the partial pressure of oxygen in the first chamber 20 can be detected by measuring the voltage VO generated on the basis of the Nernst's equation, by using a voltmeter 36. The detected value of the partial pressure of oxygen is used to control the pumping voltage Vp0 of the variable power source 30 by the aid of a feedback control system 38. Specifically, the pumping operation effected by the main pumping cell 28 is controlled so that the partial pressure of oxygen in the atmosphere in the first chamber 20 has a predetermined value which is sufficiently low to control the partial pressure of oxygen in the second chamber 22 in the next step.

Especially, in this embodiment, when the amount of oxygen pumped out by the main pumping cell 28 is changed, and the oxygen concentration in the first chamber 20 is changed, then the terminal voltage between the reference electrode 32 and the inner pumping electrode 24 of the main pumping cell 28 is changed without any time delay (changed in real time). Therefore, it is possible to effectively suppress the oscillation phenomenon which would be otherwise caused in the feedback control system 38.

Each of the inner pumping electrode 24 and the outer pumping electrode 26 is composed of an inert material having a low catalytic activity on NOx such as NO contained in the measurement gas introduced into the first chamber 20. Specifically, the inner pumping electrode 24 and the outer pumping electrode 26 may be composed of a porous cermet electrode. In this embodiment, the electrode is composed of a metal such as Pt and a ceramic such as $ZrO_2$. Especially, it is necessary to use a material which has a weak reducing ability or no reducing ability with respect to the NO component in the measurement gas, for the inner pumping electrode 24 disposed in the first chamber 20 to make contact with the measurement gas. It is preferable that the inner pumping electrode 24 is composed of, for example, a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

Figure 2:
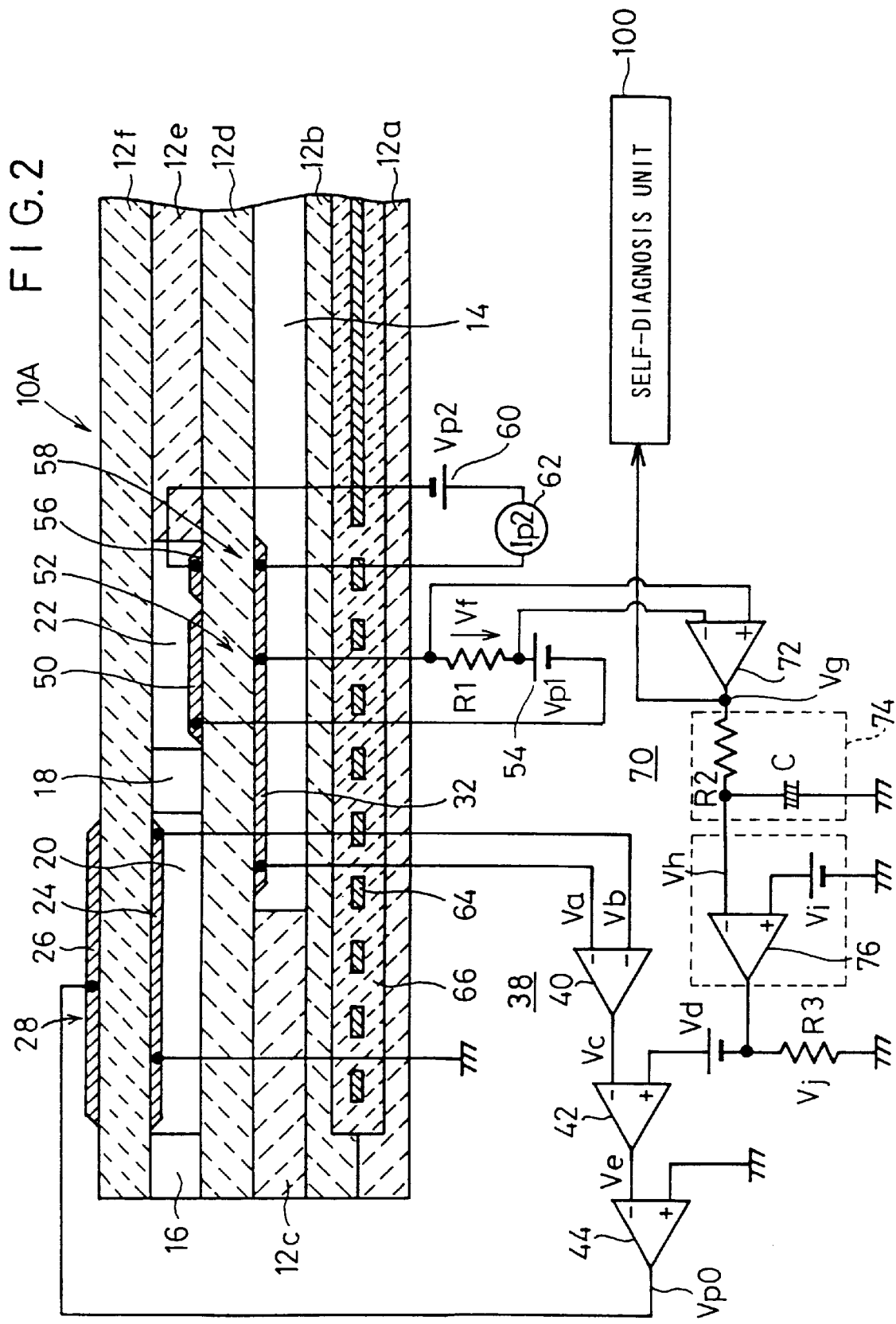
FIG. 2 shows an arrangement of a correcting control system and a feedback control system for a main pumping cell of the gas sensor according to the first embodiment.

Specifically, as shown in FIG. 2, a circuit system (feedback control system) 38 for performing the feedback control comprises a first differential amplifier 40 for determining a difference between an electric potential Va of the reference electrode 32 and an electric potential Vb of the inner pumping electrode 24, and amplifying the determined difference with a predetermined gain to make an output as a measured voltage Vc; a second differential amplifier 42 for determining a difference between the output Vc of the first differential amplifier 40 and a first reference voltage Vd, and amplifying the determined difference with a predetermined gain to make an output; and a signal-amplifying system 44 composed of a one-stage or multi-stage amplifier for amplifying the output Ve of the second differential amplifier 42 with a predetermined gain. In this embodiment, the wiring connection is made so that the output of the signal-amplifying system 44, i.e., the voltage Vp0 is supplied to the outer pumping electrode 26 of the main pumping cell 28, and the inner pumping electrode 24 is grounded. The signal-amplifying system 44, which is disposed at the final stage, serves to efficiently operate the main pumping cell 28 by amplifying the signal having the small level supplied from the previous stage with the predetermined gain.

Accordingly, at first, the measurement gas is introduced into the first chamber 20 via the first diffusion rate-determining section 16. The electric potential Va of the reference electrode 32 and the electric potential Vb of the inner pumping electrode 24 at that time are supplied to respective input terminals of the first differential amplifier 40. The first differential amplifier 40 outputs the difference (measured voltage) Vc between the electric potentials Va, Vb. The measured voltage Vc is applied, for example, to an inverting terminal of the second differential amplifier 42 disposed at the downstream stage. The second differential amplifier 42 determines the difference between the measured voltage Vc supplied to the inverting terminal and the first reference voltage Vd supplied to a non-inverting terminal. The voltage signal Ve, which is obtained by amplifying the determined difference with the predetermined gain, is outputted from an output terminal of the second differential amplifier 42. The voltage signal Ve is amplified with the predetermined gain by the signal-amplifying system 44 disposed at the downstream stage, and an obtained voltage is supplied as the pumping voltage Vp0 to the outer pumping electrode 26 of the main pumping cell 28. In this embodiment, the inner pumping electrode 24 has the ground electric potential (0 V). Therefore, the voltage between the both electrodes 24, 26 of the main pumping cell 28 is equivalent to the pumping voltage Vp0 supplied from the signal-amplifying system 44 after all.

Therefore, the main pumping cell 28 pumps out or pumps in oxygen in an amount corresponding to the level of the pumping voltage Vp0, of the measurement gas introduced into the first chamber 20. The oxygen concentration in the first chamber 20 is subjected to feedback control to give a predetermined level by repeating the series of operations described above.

On the other hand, as shown in FIG. 1, an auxiliary pumping electrode 50 having a substantially rectangular planar configuration and composed of a porous cermet electrode is formed on the entire lower surface portion for forming the second chamber 22, of the lower surface of the second solid electrolyte layer 12f. An auxiliary electrochemical pumping cell, i.e., an auxiliary pumping cell 52 is constructed by the auxiliary pumping electrode 50, the reference electrode 32, and the first solid electrolyte layer 12d.

It is preferable that the auxiliary pumping electrode 50 is composed of a material having a weak reducing ability or no reducing ability with respect to the NO component contained in the measurement gas, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au, in the same manner as the inner pumping electrode 24 of the main pumping cell 28. Further, when an alloy comprising Au and a metal of the Pt group is used as an electrode material, it is preferable to add Au in an amount of 0.03 to 35% by volume of the entire metal components. A desired constant voltage Vp1 is applied between the reference electrode 32 and the auxiliary pumping electrode 50 of the auxiliary pumping cell 52 by the aid of an external power source 54. Thus, the oxygen in the atmosphere in the second chamber 22 can be pumped out to the reference gas-introducing space 14. Accordingly, the partial pressure of oxygen in the atmosphere in the second chamber 22 is allowed to have a low value of partial pressure of oxygen at which the measurement of the amount of the objective component is not substantially affected, under the condition in which the measurement gas component (NOx) is not substantially reduced or decomposed. In this embodiment, owing to the operation of the main pumping cell 28 for the first chamber 20, the change in amount of oxygen introduced into the second chamber 22 is greatly reduced as compared with the change in the measurement gas. Accordingly, the partial pressure of oxygen in the second chamber 22 is accurately controlled to be constant.

In the gas sensor 10A according to the first embodiment, a detecting electrode 56 having a substantially rectangular planar configuration and composed of a porous cermet electrode is formed at a portion separated from the second diffusion rate-determining section 18, on an upper surface portion for forming the second chamber 22, of the upper surface of the first solid electrolyte layer 12d. An electrochemical pumping cell, i.e., a measuring pumping cell 58 is constructed by the detecting electrode 56, the reference electrode 32, and the first solid electrolyte layer 12d.

The detecting electrode 56 is composed of a porous cermet comprising zirconia as a ceramic and Rh as a metal capable of reducing NOx as the measurement gas component. Accordingly, the detecting electrode 56 functions as a NOx-reducing catalyst for reducing NOx existing in the atmosphere in the second chamber 22. Further, the oxygen in the atmosphere in the second chamber 22 can be pumped out to the reference gas-introducing space 14 by applying a constant voltage Vp2 between the detecting electrode 56 and the reference electrode 32 by the aid of a DC power source 60. The pumping current Ip2, which is allowed to flow in accordance with the pumping operation performed by the measuring pumping cell 58, is detected by an ammeter 62.

The constant voltage (DC) power source 60 can apply a voltage of a magnitude to give a limiting current to the pumping for oxygen produced during decomposition in the measuring pumping cell 58.

The gas sensor 10A according to the first embodiment further comprises a heater 64 for generating heat in accordance with electric power supply from the outside. The heater 64 is embedded in a form of being vertically interposed between the first and second substrate layers 12a, 12b. The heater 64 is provided in order to increase the conductivity of oxygen ion. A ceramic layer 66 composed of alumina or the like is formed to cover upper and lower surfaces of the heater 64 so that the heater 64 is electrically insulated from the substrate layers 12a, 12b.

As shown in FIG. 1, the heater 64 is arranged over the entire portion ranging from the first chamber 20 to the second chamber 22. Accordingly, each of the first chamber 20 and the second chamber 22 is heated to a predetermined temperature. Simultaneously, each of the main pumping cell 28, the controlling oxygen partial pressure-detecting cell 34, the auxiliary pumping cell 52, and the measuring pumping cell 58 is also heated to a predetermined temperature and maintained at that temperature.

The gas sensor 10A according to the first embodiment further comprises a correcting control system 70 for correcting and controlling the feedback control system 38 of the main pumping cell 28 on the basis of the value of the pumping current Ip1 flowing through the auxiliary pumping cell 52.

As shown in FIG. 2, the correcting control system 70 comprises a resistor R1 inserted and connected between the DC power source 54 and the reference electrode 32 for converting the pumping current Ip1 flowing through the auxiliary pumping cell 52 into a voltage signal Vf, an amplifier 72 for amplifying the voltage signal Vf with a predetermined gain to make an output as an auxiliary pumping voltage Vg, an electrolytic capacitor C, and a resistor R2. The correcting control system 70 further comprises an integrating circuit (low-pass filter) 74 for stably operating the correcting control system 70 connected to the feedback control system 38, a third differential amplifier 76 for determining a difference between an output voltage Vh supplied from the integrating circuit 74 and a second reference voltage Vi and amplifying the determined difference with a predetermined gain, and a resistor R3 for converting an output current supplied from the third differential amplifier 76 into a voltage signal (correcting voltage) Vj to be superimposed on the first reference voltage Vd used for the feedback control system 38. The second reference voltage Vi is set to be a voltage corresponding to the desired (constant) oxygen concentration in the second chamber 22.

In this description, the relationship between the pumping current flowing through the auxiliary pumping cell 52 and the voltage appearing on the resistor R1 is conveniently defined as follows.

When the oxygen concentration in the second chamber 22 is higher than a prescribed concentration (represented by a concentration higher than a desired constant level to some extent), and a large amount of oxygen is pumping-processed by the auxiliary pumping cell 52, then a large amount of pumping current flows through the resistor R1. Under this condition, the voltage is increased in the positive direction. The value of the pumping current is decreased as the oxygen concentration in the second chamber 22 is gradually lowered in accordance with the pumping process effected by the main pumping cell 28 and the auxiliary pumping cell 52. The voltage Vf is also decreased during this process.

The operation of the correcting control system 70 will now be briefly explained. At first, the pumping current Ip1 flowing through the auxiliary pumping cell 52, i.e., the oxygen concentration in the second chamber 22 is detected by the aid of the resistor R1 inserted and connected between the reference electrode 32 and the DC power source 54 of the auxiliary pumping cell 52, which is outputted as the voltage signal Vf corresponding to the oxygen concentration.

The voltage signal Vf is amplified with the predetermined gain to give the auxiliary pumping voltage Vg by means of the amplifier 72 disposed at the downstream stage. The auxiliary pumping voltage Vg is processed by the integrating circuit 74 disposed at the downstream stage to give the output voltage Vh which is inputted into the third differential amplifier 76 disposed at the downstream stage.

The integrating circuit 74 has its circuit constants (resistance value and capacitance value) which are set to give a time constant corresponding to the delay time depending on the diffusion resistance of the second diffusion rate-determining section 18. Accordingly, the integrating operation is added to the control operation effected by the correcting control system 70. The oscillation phenomenon in the correcting control system 70, which would be otherwise caused by disturbance or the like, is effectively avoided. Thus, the control operation is stably performed.

The third differential amplifier 76 determines the difference between the second reference voltage Vi and the output voltage Vh supplied from the integrating circuit 74 disposed at the upstream stage. The current (current in the positive or negative direction) corresponding to the determined difference is allowed to flow on the output side. The current flows through the resistor R3. Voltage drop occurs during this process to make conversion into the correcting voltage Vj corresponding to the current value. The correcting voltage Vj is superimposed on the first reference voltage Vd.

The correcting operation performed by the correcting control system 70 for the first reference voltage Vd allows the second differential amplifier 42 of the feedback control system 38 to determine a difference between the voltage Vc based on the partial pressure of oxygen in the first chamber 20 and a new reference voltage {first reference voltage Vd+(difference between auxiliary pumping voltage Vh and second reference voltage Vi)}. The oxygen concentration in the second chamber 22 is reflected (superimposed) as the correcting voltage Vj onto the first reference voltage Vd. That is, the second differential amplifier 42 has a function to vary and modulate the oxygen concentration in the first chamber 20 depending on the pumping current Ip1 flowing through the auxiliary pumping cell 52.

The correcting operation, which is effected for the first reference voltage Vd by the correcting control system 70, provides a constant oxygen concentration in the second chamber 22. Accordingly, it is possible to avoid the deterioration of accuracy which would be otherwise caused by leakage and invasion of oxygen brought about by large change in oxygen concentration in the measurement gas. Further, it is possible to avoid the deterioration of accuracy which would be otherwise involved in slight decomposition of $H_2O$ brought about by increase in concentration of $H_2O$ in the measurement gas. Moreover, it is possible to avoid the occurrence of the two types of deterioration of accuracy which would be otherwise caused by temperature change as well as the occurrence of the two types of deterioration of accuracy which would be otherwise caused by deterioration of the main pumping cell 28. Especially, as shown in FIG. 1, the gas sensor 10A according to the first embodiment includes a self-diagnosis unit 100 for monitoring the condition of the gas sensor 10A, the self-diagnosis unit 100 being connected downstream from the auxiliary pumping cell 52.

Specifically, as shown in FIG. 2, an output line of the amplifier 72 is branched into two. One output line is connected to one terminal of the resistor R2 of the integrating circuit, and the other output line is connected to the self-diagnosis unit 100.

Figure 3:
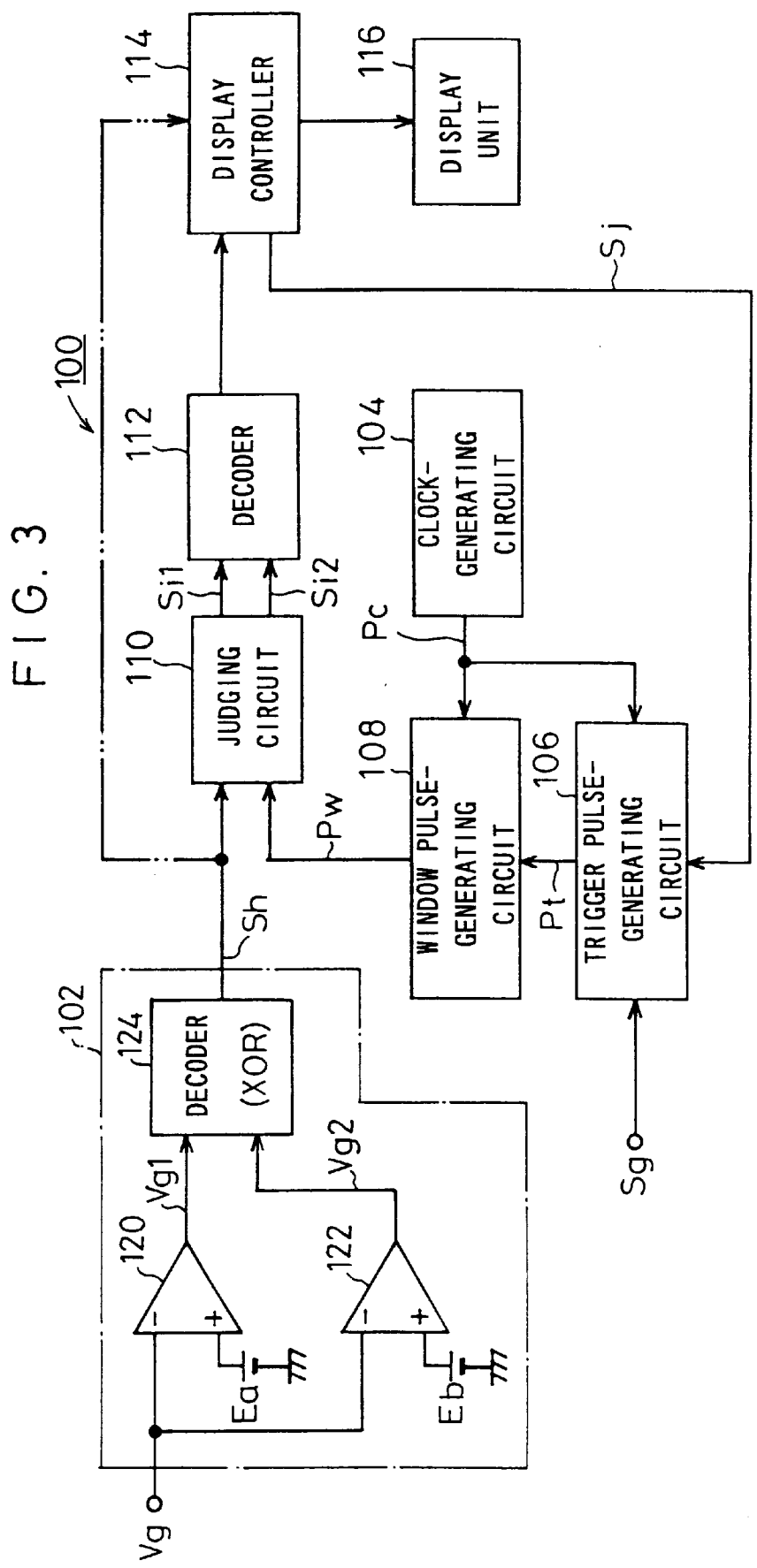
FIG. 3 shows a block diagram illustrating a specified example of a self-diagnosis unit connected to the gas sensor according to the first embodiment.

As shown in FIG. 3, the self-diagnosis unit 100 comprises a comparator circuit 102 for comparing the level of the voltage signal Vg supplied from the amplifier 72 with a predetermined prescribed range (upper limit level Ea to lower limit level Eb), a clock-generating unit 104 for generating a predetermined clock Pc, a trigger pulse-generating circuit 106 for generating a trigger pulse signal Pt on the basis of an input of an instruction signal Sg supplied, for example, from an unillustrated microcomputer installed outside, a window pulse-generating circuit 108 for generating a window pulse Pw having a predetermined pulse width on the basis of an input of the trigger pules signal Pt supplied from the trigger pulse-generating circuit 106, a judging circuit 110 for judging whether or not the level of the voltage signal Vg arrives at the prescribed range (level Ea to Eb) within the pulse width of the window pulse Pw outputted from the window pulse-generating circuit 108, a decoder 112 for analyzing a result of judgement supplied from the judging circuit 110 to make an output as a display control signal, and a display controller 114 for outputting, to a display unit 116, a display signal or display data corresponding to an attribute of the control signal supplied from the decoder 112.

The comparator circuit 102 comprises a first comparator 120 for comparing the level of the voltage signal Vg supplied from the amplifier 72 with the upper limit level Ea, a second comparator 122 for comparing the level of the voltage signal Vg supplied from the amplifier 72 with the lower limit level Eb, and a decoder 124 for performing predetermined logical operation {for example, exclusive OR (XOR)} for the outputs from the first and second comparators 120, 122 to make an output as a comparison result signal Sh.

The voltage signal Vg1 outputted from the first comparator 120 is at a low level if the level of the voltage signal Vg is higher than the upper limit level Ea. The voltage signal Vg1 is at a high level if the level of the voltage signal Vg is lower than the upper limit level Ea.

The voltage signal Vg2 outputted from the second comparator 122 is at a low level if the level of the voltage signal Vg is higher than the lower limit level Eb. The voltage signal Vg2 is at a high level if the level of the voltage signal Vg is lower than the lower limit level Eb.

The comparison result signal Sh outputted from the decoder 124 is at a low level if both of the voltage signals Vg1, Vg2 are at high levels or low levels (namely if the level of the voltage signal Vg is without the prescribed range). The comparison result signal Sh is at a high level if the voltage signal Vg1 is at a high level and the voltage signal Vg2 is at a low level (namely if the level of the voltage signal Vg is within the prescribed range).

On the other hand, the trigger pulse-generating circuit 106 is in an enable state, for example, on the basis of the input of the instruction signal Sg from the outside, and it generates one trigger pulse Pt, for example, at an initial rising timing of an clock Pc. Thereafter, the trigger pulse-generating circuit 106 generates the trigger pulse Pt every time when a predetermined number of clocks are counted.

Figure 4:
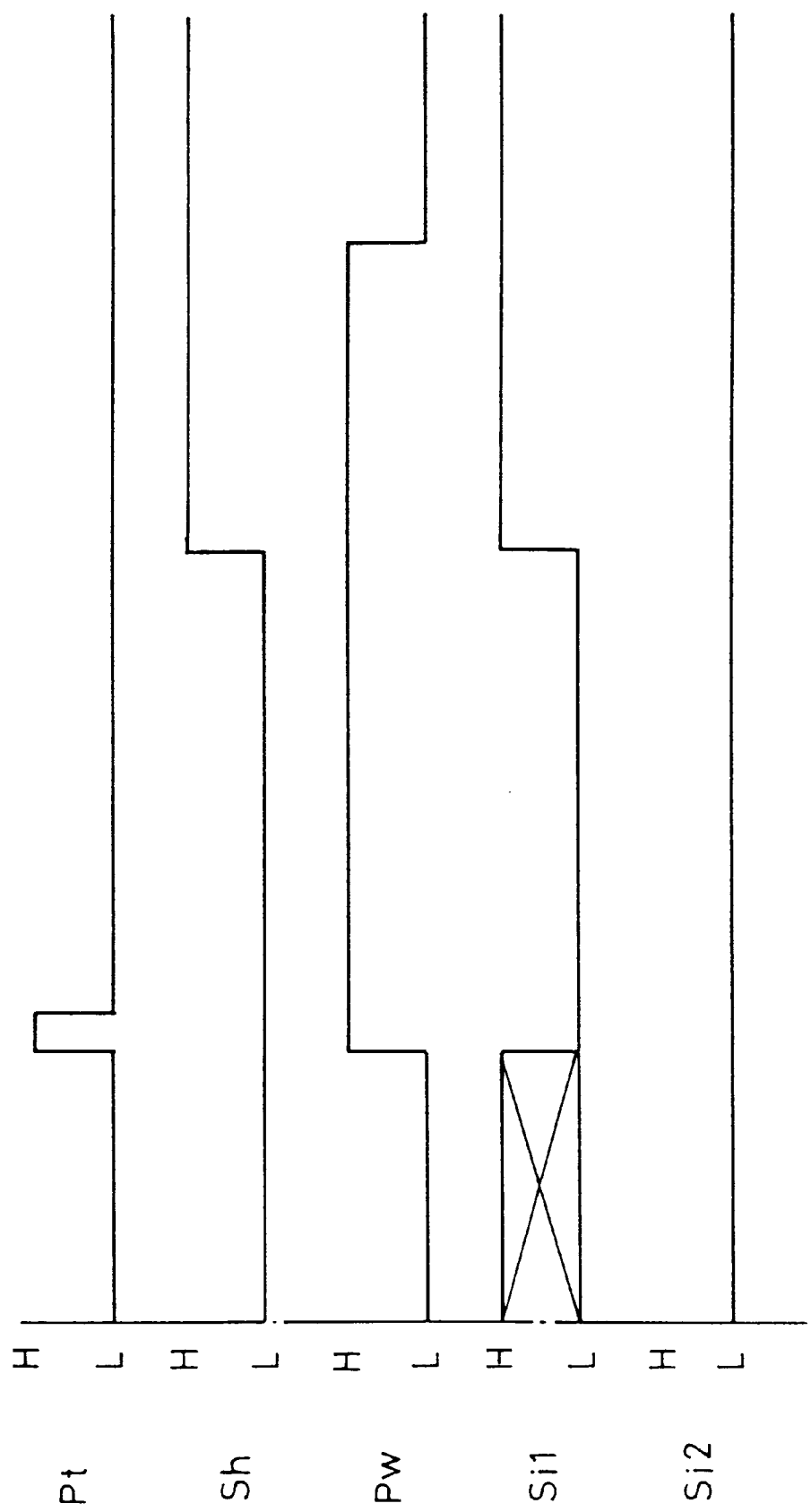
FIG. 4 shows a timing chart illustrating an example of signal processing effected by the self-diagnosis unit when the gas sensor is normally operated.
Figure 5:
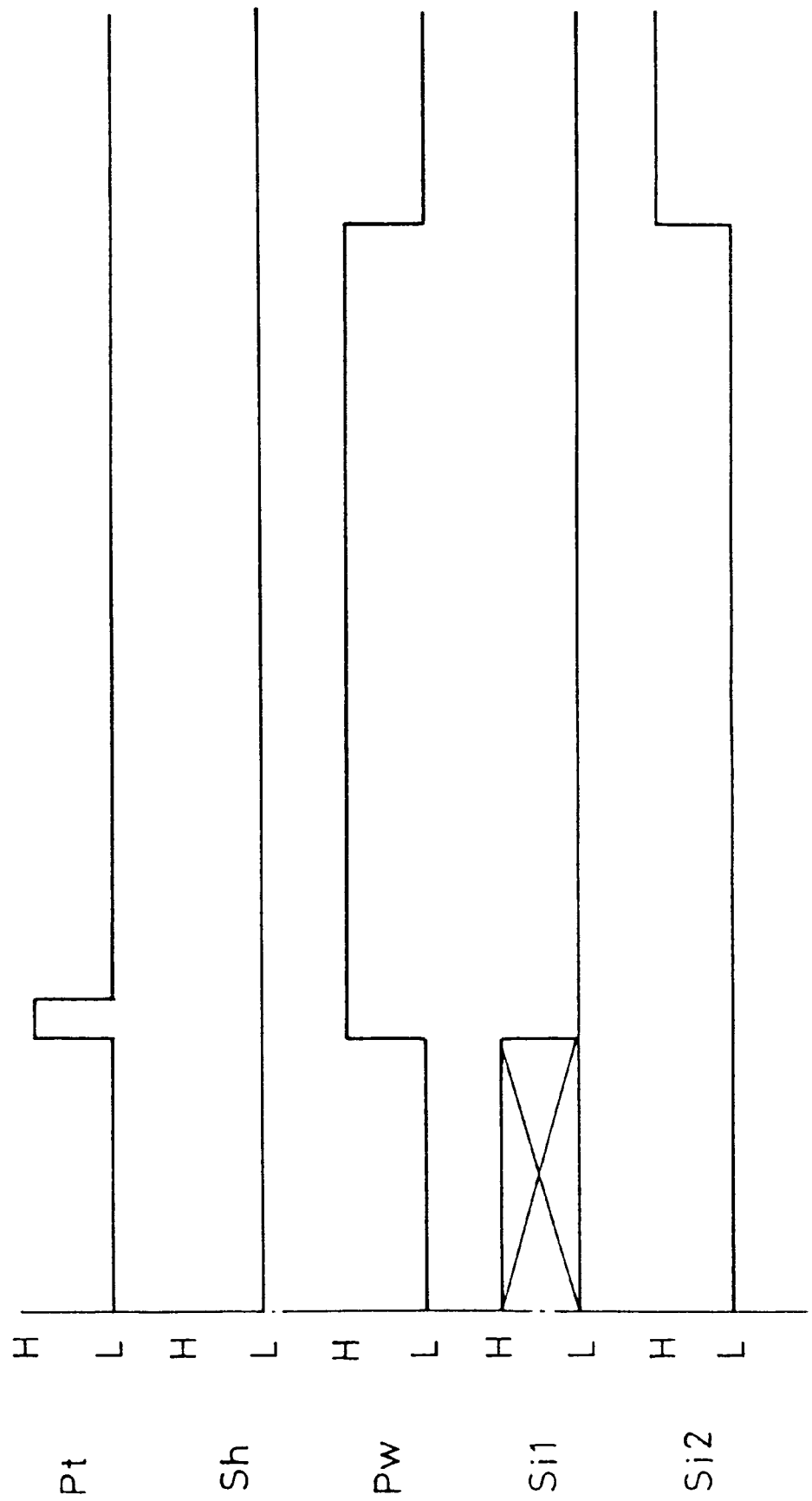
FIG. 5 shows a timing chart illustrating an example of signal processing effected by the self-diagnosis unit when the gas sensor is abnormally operated.

The window pulse-generating circuit 108 is in an enable state on the basis of the input of the trigger pulse Pt supplied from the trigger pulse-generating circuit 106, and it generates, for example, one window pulse Pw which rises at the initial rising timing of the clock Pc and which falls at a point of time at which a predetermined number of clocks are counted (see FIGS. 4 and 5).

The judging circuit 110 outputs two types of judgement signals (first and second judgement signals Si1, Si2) depending on the change in level of the window pulse Pw and the output signal Sh from the comparator circuit 102.

As shown in FIG. 4, for example, the first judgement signal Si1 is at a low level if the output signal Sh from the comparator circuit 102 is at a low level at the point of time of rising of the window pulse Pw, and it is at a high level if the output signal Sh from the comparator circuit 102 is at a high level within the pulse width of the window pulse Pw. Therefore, if the output signal from the comparator circuit 102 is not at the high level within the pulse width of the window pulse Pw, that is, if the level of the voltage signal Vf is not within the prescribed range, then the first judgement signal Si1 maintains the low level.

As shown in FIG. 5, for example, the second judgement signal Si2 is at the high level at the point of time of completion of the window pulse Pw (at the point of falling thereof) if the first judgement signal Si1 is at the low level.

The decoder 112 outputs a control signal (for example, a low level signal) for indicating "normal" to the display controller 114 disposed downstream if the first and second judgement signals Si1, Si2 are at the high level and the low level respectively. The decoder 112 outputs a control signal (for example, a high level signal) for indicating "abnormal" to the display controller 114 disposed downstream if the first and second judgement signals Si1, Si2 are at the low level and the high level respectively.

The display controller 114 outputs, to the display unit 116 disposed downstream, information indicating "normals", for example, display data for message or symbol to indicate "normal" if the control signal fed from the decoder 112 indicates "normal". When the display unit 116 is, for example, an LED (light emitting diode), the display controller 114 outputs, for example, a signal indicating light-out.

On the other hand, the display controller 114 outputs information indicating "abnormal", for example, display data for message or symbol to indicate "abnormal" if the control signal fed from the decoder 112 indicates "abnormal". When the display unit 116 is, for example, an LED (light emitting diode), the display controller 114 outputs, for example, a signal indicating light-up.

If the control signal indicating "abnormal" is supplied from the decoder 112 disposed upstream, the display controller 114 outputs a disable signal Sj to the trigger pulse-generating circuit 106 so that the trigger pulse-generating circuit 106 is in a stopped state.

The gas sensor 10A according to the first embodiment is basically constructed as described above. Next, its function and effect, especially function and effect of the self-diagnosis unit 100 will be explained.

At first, when the power source is turned on for the apparatus installed with the gas sensor 10A, the initial operation is performed in the apparatus. The initial operation includes electric power application to the heater 64 of the gas sensor 10A.

At a point of time after passage of a predetermined period of time (for example, a period of time for completing the warming-up process for the gas sensor 10A) from the point of time of the electric power application to the heater 64, the microcomputer (not shown) outputs the instruction signal Sg to the trigger pulse-generating circuit 106 of the self-diagnosis unit 100. When the apparatus for installing the gas sensor 10A therein is an automobile, the point of time of the completion of the warming-up process indicates a point of time at which the water temperature arrives at a predetermined value.

From the point of time at which the instruction signal Sg is supplied from the microcomputer (not shown) to the self-diagnosis unit 100, the self-diagnosis unit 100 starts monitoring for the gas sensor 10A, i.e., monitoring for the pumping current Ip1 flowing through the auxiliary pumping cell 52. In the first embodiment, the monitoring is performed for the voltage signal Vf which appears in the resistor R1 in accordance with the pumping current Ip1 flowing through the auxiliary pumping cell 52. As shown in FIG. 4, if the value of the pumping current flowing through the auxiliary pumping cell 52 (level of the voltage signal Vf) arrives at the prescribed range (within the range from the upper limit level Ea to the lower limit level Eb) within the predetermined period of time (within the pulse width of the window pulse Pw), the first and second judgement signals Si1, Si2 outputted from the judging circuit 110 are at the high level and the low level respectively. Therefore, the control signal indicating "normal" is outputted from the decoder 112. As a result, the display unit 116 makes a display indicating "normal".

After that, the instruction signal Sg is periodically supplied from the microcomputer (not shown) to the self-diagnosis unit 100. Self-diagnosis for the gas sensor 10A is performed every time when the instruction signal Sg is supplied.

On the other hand, as shown in FIG. 5, if the level of the voltage signal Vg does not arrive at the prescribed range after passage of the predetermined period of time, the judging circuit 110 outputs the fist judgement signal Si1 at the low level and the second judgement signal Si2 at the high level respectively. Accordingly, the control signal indicating "abnormal" is outputted from the decoder 112, and the display unit 116 makes a display indicating "abnormal". Upon the judgement of abnormality, the disable signal Sj is outputted from the display controller 114 to the trigger first embodiment, it is possible to promptly and reliably detect whether or not the gas sensor 10A is in a failure state at present. Therefore, it is possible to make quick response to maintain and manage the gas sensor 10A (including response to legislation).

The trouble or failure of the gas sensor 10A includes, for example, failure of the main pumping cell 28 or the auxiliary pumping cell 52 itself, disconnection of the feedback control system 38 or the heater 64, and malfunction of the electrode. The malfunction of the electrode is exemplified by exhaustion and peeling-off of the electrode due to thermal damage, and decrease in catalytic activity of the electrode due to, for example, poisoning and clogging.

The self-diagnosis unit 100 judges that any trouble occurs when the voltage signal Vg supplied from the amplifier 72 does not arrive at the prescribed range even after passage of the predetermined period of time. Alternatively, the self-diagnosis unit 100 may judge that any trouble occurs, at a point of time at which the voltage signal Vg supplied from the amplifier 72 is deviated from the prescribed range. In this embodiment, the wiring connection is preferably made as follows. That is, the comparison result signal Sh supplied from the decoder 124 in the comparator circuit 102 is directly inputted into the display controller 114 (see two-dot chain line). Further, the circuit is constructed and assembled such that the display controller 114 outputs information to indicate pulse-generating circuit 106. The process for judging the trouble to be performed by the self-diagnosis unit 100 thereafter is completed. The display indicating "abnormal" is made until the reset input is made for the display unit 116.

In general, the main pumping cell 28 of the gas sensor 10A is operated as follows. That is, the oxygen, which is contained in the measurement gas introduced from the external space into the first chamber 20, is pumping-processed in accordance with the control operation effected by the feedback control system 38 as described above. Thus, the value of the partial pressure of oxygen in the first chamber 20 is allowed to have the predetermined value at which the NO component as the measurement objective is not decomposable.

Therefore, if the oxygen concentration in the second chamber 22 cannot arrive at the prescribed level, namely if the pumping current Ip1 flowing through the auxiliary pumping cell 52 does not arrive at the prescribed range (the voltage signal Vg does not arrive at the prescribed range), although the feedback control system 38 is subjected to the correcting control by the aid of the correcting control system 70, then the gas sensor 10A has any trouble due to any cause. In the first embodiment, it is decided whether or not any trouble occurs in the gas sensor 10A by utilizing the foregoing principle.

As a result, in the gas sensor 10A according to the "normal" to the display unit 116 disposed downstream if the inputted comparison result signal Sh is at the high level, while the display controller 114 outputs information to indicate "abnormal" to the display unit 116 disposed downstream if the inputted comparison result signal Sh is at the low level.

Alternatively, the display controller 114 may be circuited and constructed as follows. That is, in the initial stage, it is monitored whether or not the voltage signal Vg arrives at the prescribed range within the predetermined period through the passage of comparator circuit 102→judging circuit 110→decoder 112→display controller 114. After it is judged that no trouble occurs, it is monitored whether or not the voltage signal Vg arrives at the prescribed range within the predetermined period in real time through the passage of comparator circuit 102→display controller 114 (see two-dot chain line).

Next, two modified embodiments of the gas sensor 10A according to the first embodiment will be described with reference to FIGS. 6 and 7. Components or parts corresponding to those shown in FIG. 1 are designated by the same reference numerals, duplicate explanation of which will be omitted.

Figure 6:
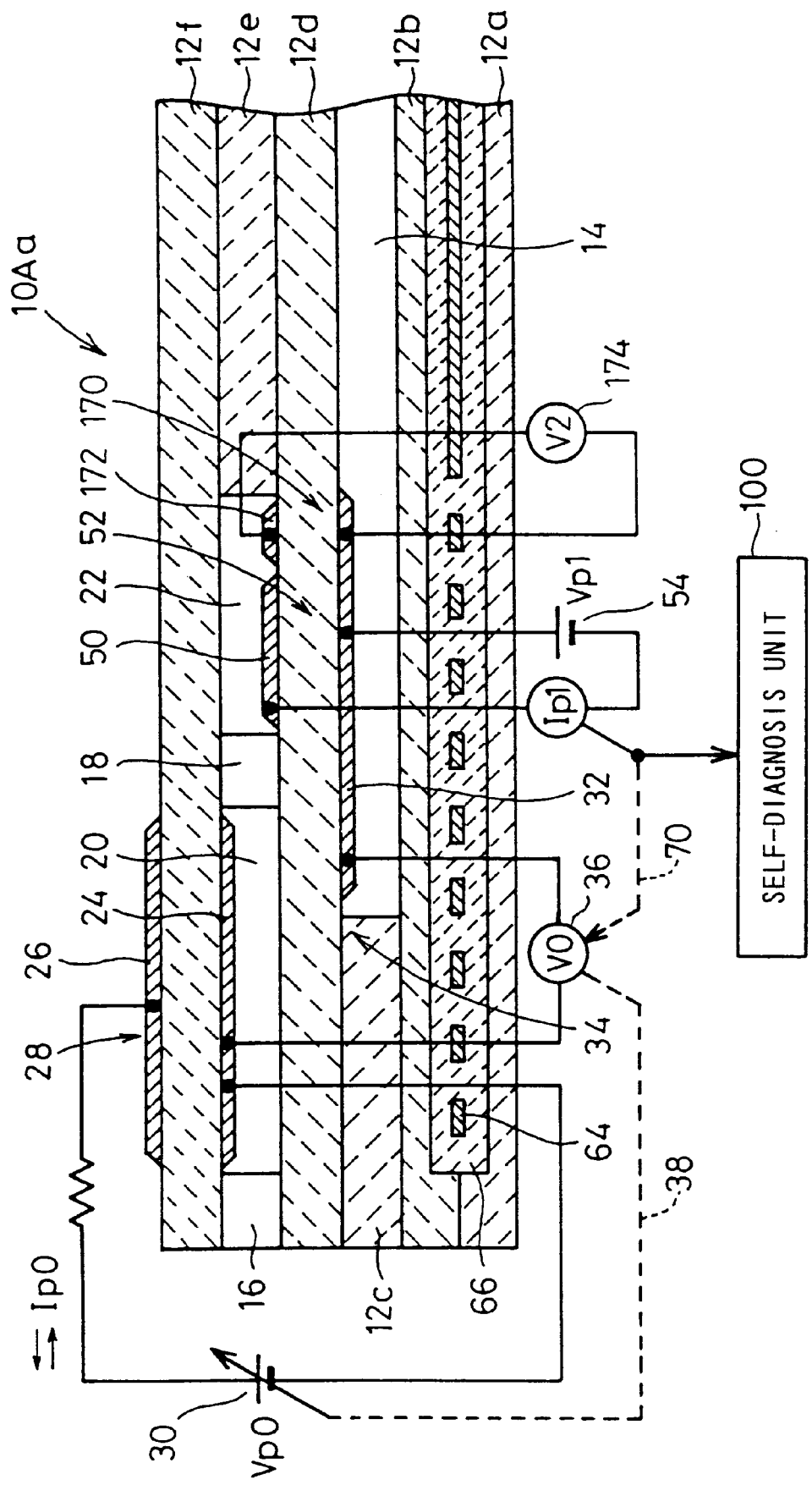
FIG. 6 shows a cross-sectional view illustrating a first modified embodiment of the gas sensor according to the first embodiment.

At first, as shown in FIG. 6, a gas sensor 10A*a* according to the first modified embodiment is constructed in approximately the same manner as the gas sensor 10A according to the first embodiment. However, the former is different from the latter in that a measuring oxygen partial pressure-detecting cell 170 is provided in place of the measuring pumping cell 58.

The measuring oxygen partial pressure-detecting cell 170 comprises a detecting electrode 172 formed on an upper surface portion for forming the second chamber 22, of the upper surface of the first solid electrolyte layer 12*d*, the reference electrode 32 formed on the lower surface of the first solid electrolyte layer 12*d*, and the first solid electrolyte layer 12*d* interposed between the both electrodes 172, 32.

In this embodiment, an electromotive force (electromotive force of an oxygen concentration cell) corresponding to the difference in oxygen concentration between the atmosphere around the detecting electrode 172 and the atmosphere around the reference electrode 32 is generated between the reference electrode 32 and the detecting electrode 172 of the measuring oxygen partial pressure-detecting cell 170.

Therefore, the partial pressure of oxygen in the atmosphere around the detecting electrode 172, in other words, the partial pressure of oxygen defined by oxygen produced by reduction or decomposition of the measurement gas component (NOx) is detected as a voltage value by measuring the electromotive force generated between the detecting electrode 172 and the reference electrode 32 by using a voltmeter 174.

The gas sensor 10A*a* according to the first modified embodiment also comprises the feedback control system 38, the auxiliary pumping cell 52, the correcting control system 70, and the self-diagnosis unit 100, in the same manner as the gas sensor 10A according to the first embodiment.

Therefore, it is also possible for the gas sensor 10A*a* according to the first modified embodiment to avoid the deterioration of accuracy which would be otherwise caused by leakage and invasion of oxygen brought about by large change in oxygen concentration in the measurement gas. Further, it is possible to avoid the deterioration of accuracy which would be otherwise involved in slight decomposition of $H_2O$ brought about by increase in concentration of $H_2O$ in the measurement gas, in the same manner as the gas sensor 10A according to the first embodiment. Moreover, it is possible to promptly and reliably detect whether or not the gas sensor 10A*a* is in a failure state at present. Therefore, it is possible to make quick response to maintain and manage the gas sensor 10A*a*.

Figure 7:
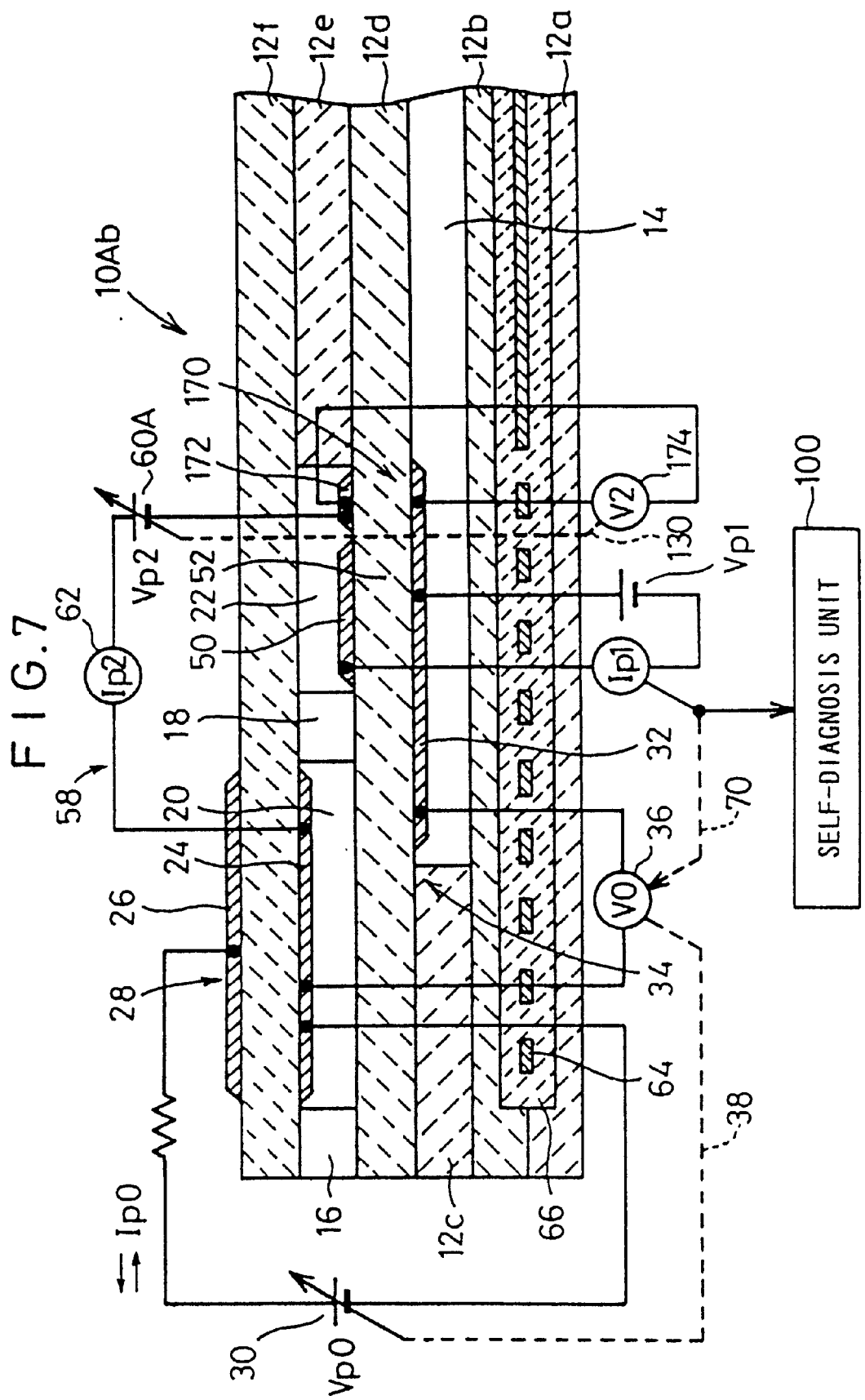
FIG. 7 shows a cross-sectional view illustrating a second modified embodiment of the gas sensor according to the first embodiment.

Next, a gas sensor 10A*b* according to the second modified embodiment shown in FIG. 7 is constructed in approximately the same manner as the gas sensor 10A*a* according to the first modified embodiment. However, the former is different from the latter in that both of the measuring pumping cell 58 and the measuring oxygen partial pressure-detecting cell 170 are provided, and the value of partial pressure of oxygen (voltage V2) detected by the measuring oxygen partial pressure-detecting cell 170 is used to control the pumping voltage Vp2 of a variable power source 60A of the measuring pumping cell 58 by the aid of the feedback control system 130.

In this embodiment, the measuring pumping cell 58 comprises the detecting electrode 172, the inner pumping electrode 24, the first solid electrolyte layer 12*d* between the both electrodes 172, 24, the second spacer layer 12*e*, and the second solid electrolyte layer 12*f*. The oxygen in the atmosphere in the second chamber 22 can be pumped out to the first chamber 20 by applying the voltage Vp2 by the aid of the variable power source 60A.

The gas sensor 10A*b* according to the second modified embodiment also comprises the feedback control system 38, the auxiliary pumping cell 52, the correcting control system 70, and the self-diagnosis unit 100, in the same manner as the gas sensor 10A according to the first embodiment. Therefore, it is possible to avoid the deterioration of accuracy which would be otherwise caused by leakage and invasion of oxygen brought about by large change in oxygen concentration in the measurement gas. Further, it is possible to avoid the deterioration of accuracy which would be otherwise involved in slight decomposition of $H_2O$ brought about by increase in concentration of $H_2O$ in the measurement gas. Moreover, it is possible to promptly and reliably detect whether or not the gas sensor 10A$b$ is in a failure state at present. Therefore, it is possible to make quick response to maintain and manage the gas sensor 10A$b$.

In the gas sensors according to the first embodiment (including the several modified embodiments) 10A, 10A$a$, 10A$b$, the output signal Vg, which is supplied from the amplifier 72 for amplifying, with the predetermined gain, the voltage signal Vf obtained by converting the pumping current Ip1 into the voltage, is inputted into the self-diagnosis unit 100. Alternatively, the output signal Vh after passing through the integrating circuit 74 may be inputted into the self-diagnosis unit 100. In this embodiment, the signal Vh, from which the high pass noise is removed, is inputted into the self-diagnosis unit 100. Therefore, it is possible to perform the self-diagnosis more accurately.

Next, a gas sensor 10B according to the second embodiment will be explained with reference to FIG. 8. Components or part corresponding to those shown in FIG. 1 are designated by the same reference numerals, duplicate explanation of which will be omitted.

Figure 8:
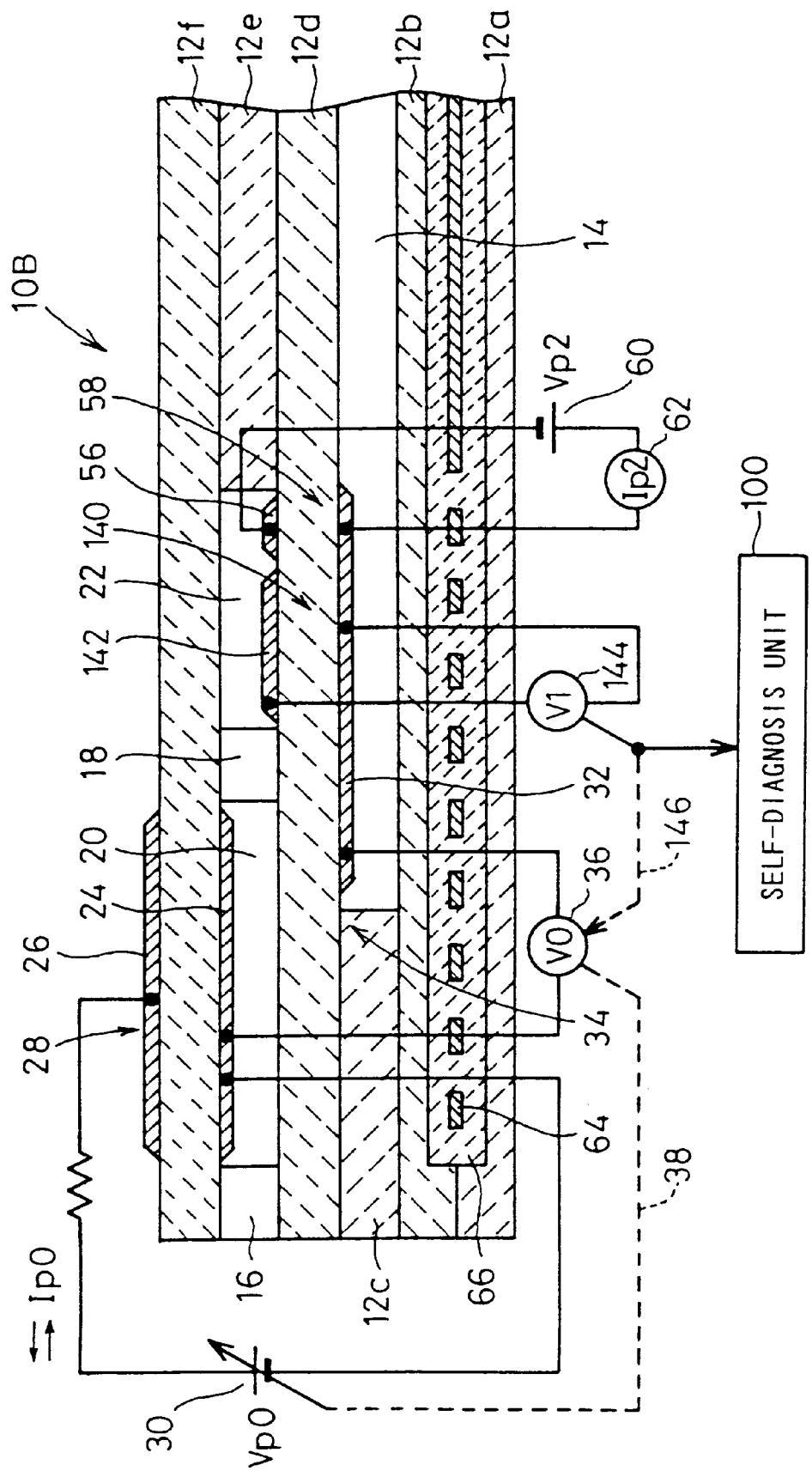
FIG. 8 shows a cross-sectional view illustrating a gas sensor according to a second embodiment.

As shown in FIG. 8, the gas sensor 10B according to the second embodiment is constructed in approximately the same manner as the gas sensor 10A according to the first embodiment. However, the former is different from the latter in that a correcting oxygen partial pressure-detecting cell 140 is provided in place of the auxiliary pumping cell 52, and a correcting control system 146 is provided for correcting and controlling the feedback control system 38 of the main pumping cell 28 on the basis of a voltage value V1 detected by the correcting oxygen partial pressure-detecting cell 140.

The correcting oxygen partial pressure-detecting cell 140 comprises a measuring electrode 142 formed on an upper surface portion for forming the second chamber 22, of the upper surface of the first solid electrolyte layer 12$d$, the reference electrode 32 formed on the lower surface of the first solid electrolyte layer 12$d$, and the first solid electrolyte layer 12$d$ interposed between the both electrodes 142, 32.

In this embodiment, an electromotive force (electromotive force of an oxygen concentration cell) corresponding to the difference in oxygen concentration between the atmosphere in the second chamber 22 and the atmosphere around the reference electrode 32 is generated between the reference electrode 32 and the measuring electrode 142 of the correcting oxygen partial pressure-detecting cell 140.

Therefore, the partial pressure of oxygen in the atmosphere around the measuring electrode 142, in other words, the partial pressure of oxygen in the second chamber 22 is detected as a voltage value by measuring the electromotive force generated between the measuring electrode 142 and the reference electrode 32 by using a voltmeter 144.

Figure 9:
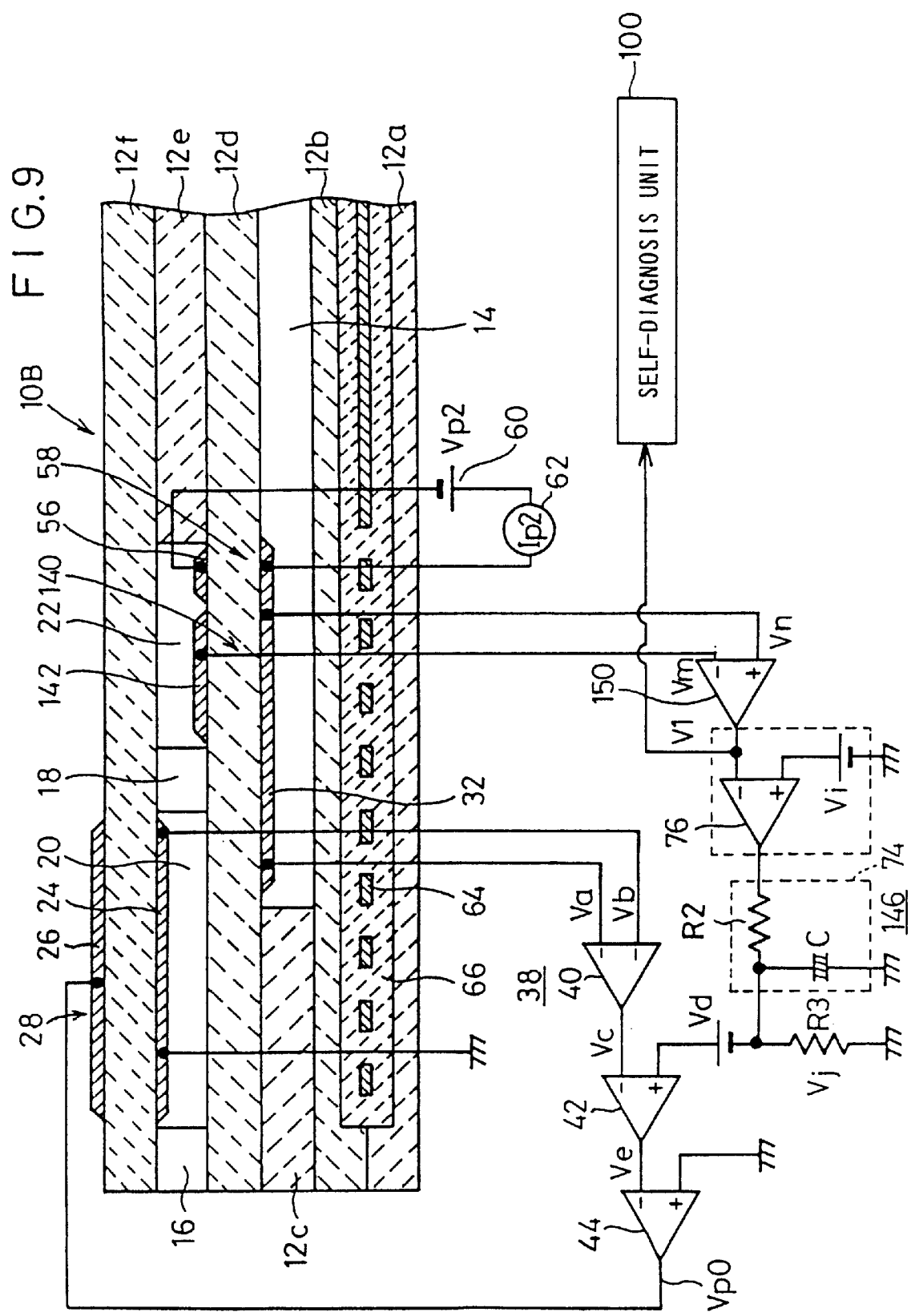
FIG. 9 shows an arrangement of a correcting control system and a feedback control system for a main pumping cell of the gas sensor according to the second embodiment.

On the other hand, as shown in FIG. 9, the correcting control system 146 comprises a fourth differential amplifier 150 for determining a difference between a difference (measured voltage Vm) between an electric potential of the measuring electrode 142 and the ground electric potential and a difference (reference voltage Vn) between an electric potential of the reference electrode 32 and the ground electric potential and amplifying the determined difference with a predetermined gain to make an output as a detection voltage V1 corresponding to the partial pressure of oxygen in the second chamber 22, a third differential amplifier 76 for determining a difference between the detection voltage V1 supplied from the fourth differential amplifier 150 and a second reference voltage Vi and amplifying the determined difference with a predetermined gain, an electrolytic capacitor C, and a resistor R2. The correcting control system 146 further comprises an integrating circuit (low-pass filter) 74 for stably operating the correcting control system 146 connected to the feedback control system 38, and a resistor R3 for converting an output current supplied from the integrating circuit 74 into a voltage signal (correcting voltage Vj) to be superimposed on the first reference voltage Vd used for the feedback control system 38.

In this description, the relationship between the value V1 and the voltage appearing on the resistor R1 is conveniently defined as follows.

When the oxygen concentration in the second chamber 22 is higher than a prescribed concentration (represented by a concentration higher than a desired constant level to some extent), the voltage detected by the correcting oxygen partial pressure-detecting cell 140 is also increased in the positive direction. The detection voltage V1 is decreased as the oxygen concentration in the second chamber 22 is gradually lowered in accordance with the pumping process effected by the main pumping cell 28.

The operation of the correcting control system 146 will now be briefly explained. At first, the fourth differential amplifier 150 is used to determine the difference between the reference voltage Vn and the measured voltage Vm obtained by the correcting oxygen partial pressure-detecting cell 140. The difference is extracted as the detection voltage V1.

The third differential amplifier 76 is used to determine the difference between the second reference voltage Vi and the detection voltage V1 supplied from the fourth differential amplifier 150. The current (current in the positive or negative direction) corresponding to the determined difference flows on the output side. The current flows through the integrating circuit 74 disposed downstream, and it flows through the resistor R3. Voltage drop occurs during this process, and the current is converted into the correcting voltage Vj corresponding to the current value. The correcting voltage Vj is superimposed on the first reference voltage Vd.

The integrating circuit 74 has its circuit constants (resistance value and capacitance value) which are set to give a time constant corresponding to the delay time depending on the diffusion resistance of the second diffusion rate-determining section 18, in the same manner as the gas sensor 10A according to the first embodiment. Accordingly, the integrating operation is added to the control operation effected by the correcting control system 146. The oscillation phenomenon in the correcting control system 146, which would be otherwise caused by disturbance or the like, is effectively avoided. Thus, the control operation is stably performed.

The correcting operation performed by the correcting control system 146 for the first reference voltage Vd allows the second differential amplifier 42 of the feedback control system 38 to determine a difference between the voltage Vc based on the partial pressure of oxygen in the first chamber 20 and a new reference voltage {first reference voltage Vd+(difference between detection voltage V1 and second reference voltage Vi)}. The oxygen concentration in the second chamber 22 is reflected (superimposed) as the correcting voltage Vj onto the first reference voltage Vd. That is, the second differential amplifier 42 has a function to vary and modulate the oxygen concentration in the first chamber 20 depending on the detection voltage V1 detected by the correcting oxygen partial pressure-detecting cell 140. The correcting operation, which is effected for the first reference voltage Vd by the correcting control system 146, provides a constant oxygen concentration in the second chamber 22. Accordingly, it is possible to avoid the deterioration of accuracy which would be otherwise caused by leakage and invasion of oxygen brought about by large change in oxygen concentration in the measurement gas. Further, it is possible to avoid the deterioration of accuracy which would be otherwise involved in slight decomposition of $H_2O$ brought about by increase in concentration of $H_2O$ in the measurement gas. Moreover, it is possible to avoid the occurrence of the two types of deterioration of accuracy which would be otherwise caused by temperature change as well as the occurrence of the two types of deterioration of accuracy which would be otherwise caused by deterioration of the main pumping cell 28.

Especially, as shown in FIG. 9, in the gas sensor 10B according to the second embodiment, an output line of the fourth differential amplifier 150 Is branched into two. One output line is connected to an inverting input terminal of the third differential amplifier 76, and the other output line is connected to a self-diagnosis unit 100. The self-diagnosis unit 100 is constructed in the same manner as the self-diagnosis unit 100 shown in FIG. 3 except that the signal, which Is inputted into the self-diagnosis unit 100 via the other output line, is the detection voltage V1 supplied from the fourth differential amplifier 150. Therefore, detailed explanation therefor will be omitted.

Therefore, as for the gas sensor 10B according to the second embodiment, it is possible to promptly and reliably detect whether or not the gas sensor 10B is in a failure state at present. Therefore, it is possible to make quick response to maintain and manage the gas sensor 10B.

Next, two modified embodiments of the gas sensor 10B according to the second embodiment will be described with reference to FIGS. 10 and 11. Components or parts corresponding to those shown in FIG. 8 are designated by the same reference numerals, duplicate explanation of which will be omitted.

Figure 10:
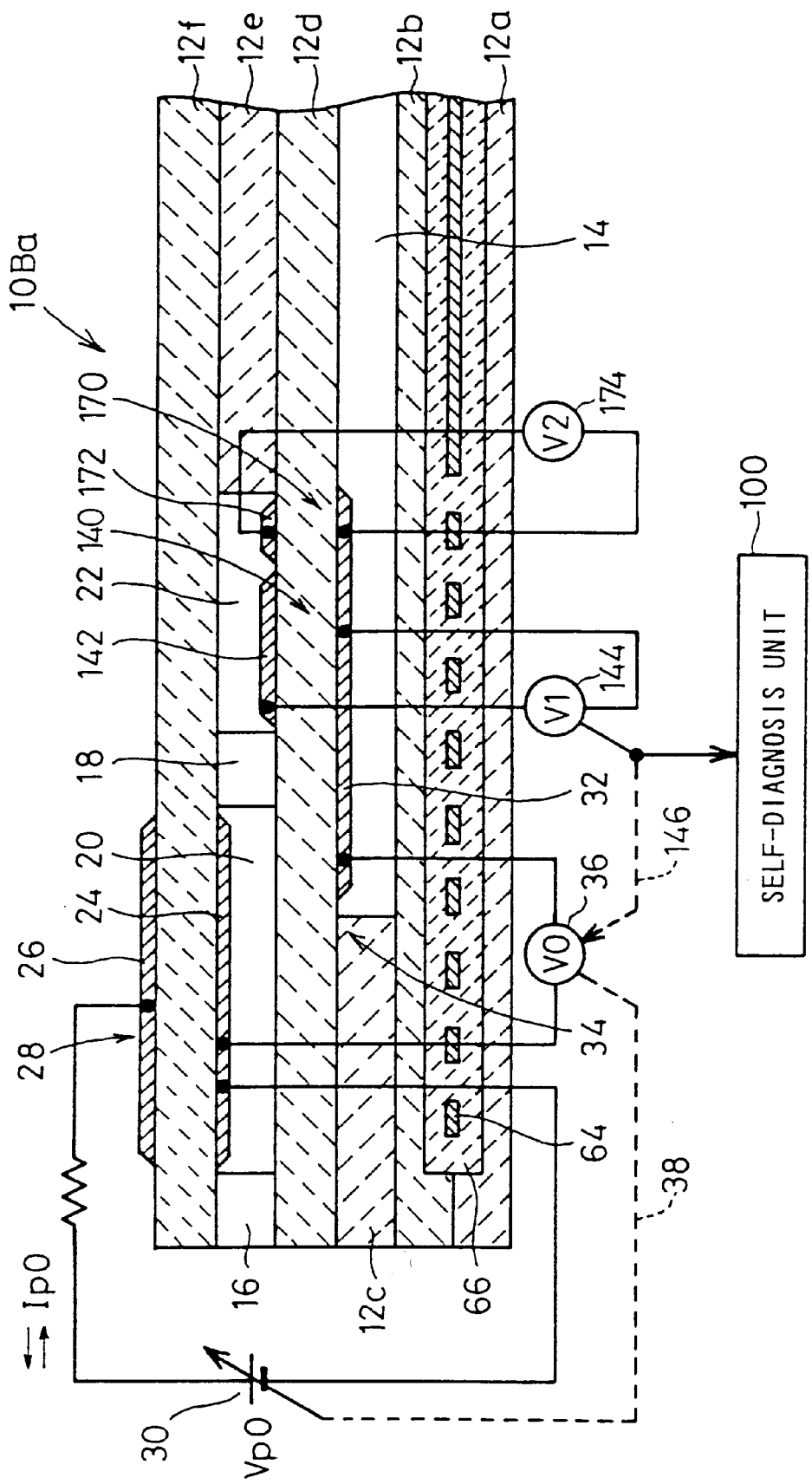
FIG. 10 shows a cross-sectional view illustrating a first modified embodiment of the gas sensor according to the second embodiment.

At first, as shown in FIG. 10, a gas sensor 10Ba according to the first modified embodiment is constructed in approximately the same manner as the gas sensor 10B according to the second embodiment. However, the former is different from the latter in that a measuring oxygen partial pressure-detecting cell 170 is provided in place of the measuring pumping cell 58.

The measuring oxygen partial pressure-detecting cell 170 is the same as the measuring oxygen partial pressure-detecting cell 170 of the gas sensor 10Aa according to the first modified embodiment concerning the first embodiment shown in FIG. 6. Therefore, detailed explanation therefor will be omitted.

The gas sensor 10Ba according to the first modified embodiment also comprises the feedback control system 38, the correcting oxygen partial pressure-detecting cell 140, the correcting control system 146, and the self-diagnosis unit 100, in the same manner as the gas sensor 10B according to the second embodiment. Accordingly, it is also possible to avoid the deterioration of accuracy which would be otherwise caused by leakage and invasion of oxygen brought about by large change in oxygen concentration in the measurement gas. Further, it is possible to avoid the deterioration of accuracy which would be otherwise involved in slight decomposition of $H_2O$ brought about by increase in concentration of $H_2O$ in the measurement gas. Moreover, it is possible to promptly and reliably detect whether or not the gas sensor 10Ba is in a failure state at present. Therefore, it is possible to make quick response to maintain and manage the gas sensor 10Ba.

Figure 11:
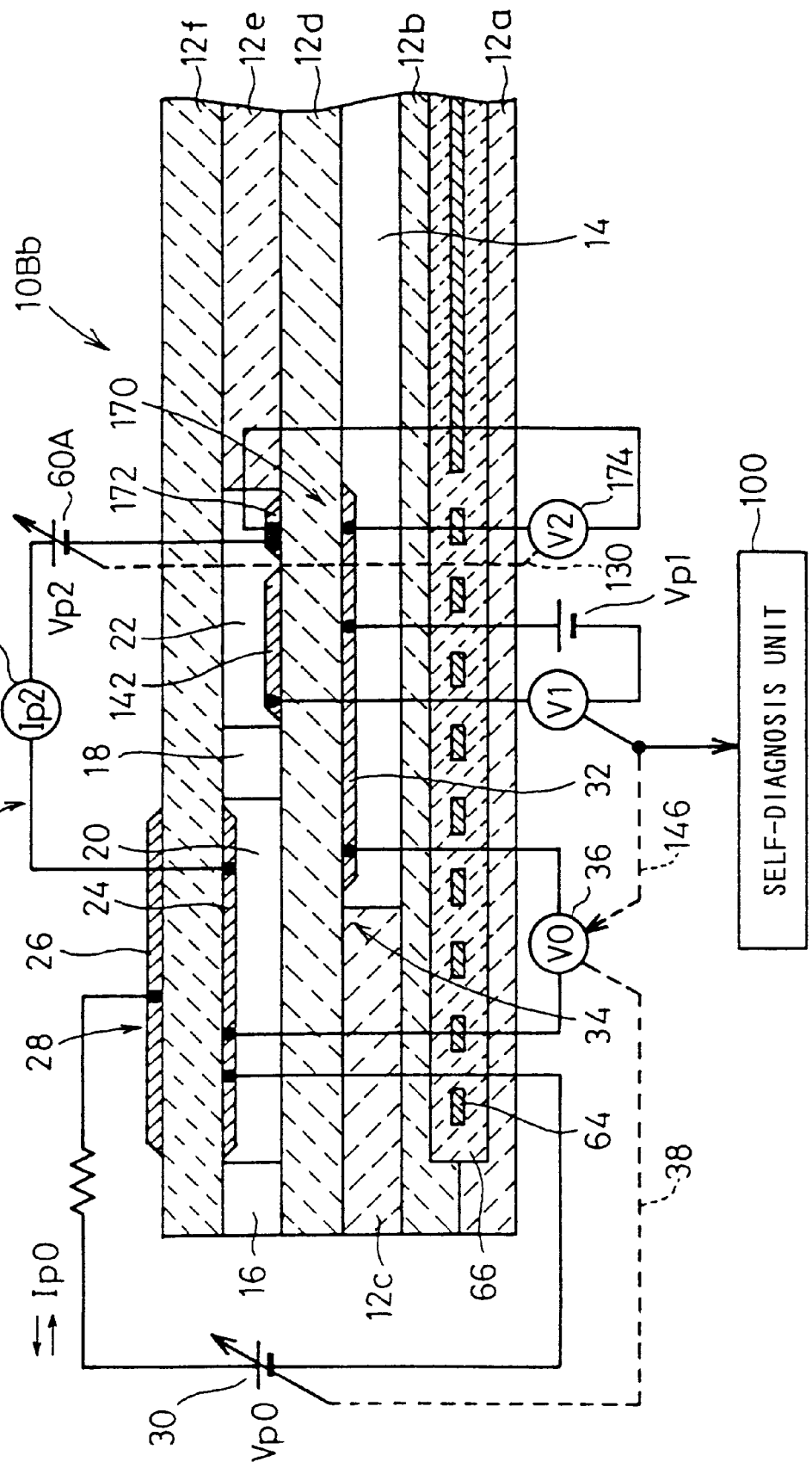
FIG. 11 shows a cross-sectional view illustrating a second modified embodiment of the gas sensor according to the second embodiment.

Next, a gas sensor 10Bb according to the second modified embodiment shown in FIG. 11 is constructed in approximately the same manner as the gas sensor 10Ba according to the first modified embodiment. However, the former is different from the latter in that both of the measuring pumping cell 58 and the measuring oxygen partial pressure-detecting cell 170 are provided, and the value of partial pressure of oxygen detected by the measuring oxygen partial pressure-detecting cell 170 is used to control the pumping voltage Vp2 of a variable power source 60A of the measuring pumping cell 58 by the aid of the feedback control system 130, in the same manner as the gas sensor 10Ab according to the second modified embodiment concerning the first embodiment shown in FIG. 7.

The gas sensor 10Bb according to the second modified embodiment also comprises the feedback control system 38, the correcting oxygen partial pressure-detecting cell 140, the correcting control system 146, and the self-diagnosis unit 100, in the same manner as the gas sensor 10B according to the second embodiment. Therefore, it is possible to avoid the deterioration of accuracy which would be otherwise caused by leakage and invasion of oxygen brought about by large change in oxygen concentration in the measurement gas. Further, it is possible to avoid the deterioration of accuracy which would be otherwise involved in slight decomposition of $H_2O$ brought about by increase in concentration of $H_2O$ in the measurement gas. Moreover, it is possible to promptly and reliably detect whether or not the gas sensor 10Bb is in a failure state at present. Therefore, it is possible to make quick response to maintain and manage the gas sensor 10Bb.

In the gas sensors according to the second embodiment (including the several modified embodiments) 10B, 10Ba, 10Bb, the voltage signal V1, which is supplied from the fourth differential amplifier 150, is inputted into the self-diagnosis unit 100. Alternatively, the voltage signal after passing through the integrating circuit 74 may be inputted into the self-diagnosis unit 100. In this embodiment, the voltage signal, from which the high pass noise is removed, is inputted into the self-diagnosis unit 100. Therefore, it is possible to perform the self-diagnosis more accurately.

In the respective second modified embodiments 10Ab, 10Bb of the gas sensors 10A, 10B according to the first and second embodiments, the one electrode of the measuring pumping cell 58 is the inner pumping electrode 24 of the main pumping cell 28. Alternatively, the one electrode may be the outer pumping electrode 26. In this case, the oxygen in the atmosphere in the second chamber 22 is pumped out to the external space.

In the gas sensors according to the first and second embodiments (including several modified embodiments) 10A, 10Aa, 10Ab, 10B, 10Ba, 10Bb, the arrangement as shown in FIG. 3 is adopted for the self-diagnosis unit 100. However, this arrangement is persistently illustrative. The gas sensor of the present invention can be constructed by using various combinations of digital and analog circuits.

The gas sensors according to the embodiments described above are directed to NOx as the measurement gas component. However, the present invention is also effectively applicable to the measurement of bound oxygen-containing gas components such as $H_2O$ and $CO_2$ other than NOx, in which the measurement is affected by oxygen existing in the measurement gas.

It is a matter of course that the present invention is not limited to the embodiments described above, which may be constructed in other various forms without deviating from the gist or essential characteristics of the present invention.

What is claimed is:

1. A gas sensor comprising:
   a main pumping means for pumping-processing oxygen contained in a measurement gas introduced from an external space into a processing space formed by solid electrolytes contacting with said external space;
   a main pumping control means for comparing a partial pressure of oxygen in said processing space with a first reference value to control said main pumping means so that said partial pressure of oxygen has a predetermined value at which a predetermined gas component as a measurement objective is not decomposable; and
   an electric signal-generating conversion means for decomposing said predetermined gas component contained in said measurement gas after being pumping-processed by said main pumping means, by the aid of a catalytic action and/or electrolysis for creating an electric signal corresponding to an amount of oxygen produced by said decomposition wherein:
   said predetermined gas component contained in said measurement gas is measured on the basis of said electric signal supplied from said electric signal-generating conversion means, said gas sensor further comprising:
      an oxygen concentration-detecting means for detecting a concentration of oxygen contained in said measurement gas after being pumping-processed by said main pumping means;
      a correcting control means for correcting and controlling said main pumping control means on the basis of a difference between a detected voltage or current value proportional to the concentration of oxygen as measured by the oxygen concentration detecting means supplied from said oxygen concentration-detecting means and a second reference value to give a constant concentration of oxygen contained in said measurement gas after being pumping-processed by said main pumping means; and
      a self-diagnosis means for comparing said detected voltage or current value supplied from said oxygen concentration-detecting means with a prescribed range to decide whether or not any abnormal condition occurs, on the basis of a result of said comparison.

2. The gas sensor according to claim 1, wherein:
   said electric signal-generating conversion means comprises a measuring pumping means for decomposing said predetermined gas component contained in said measurement gas after being pumping-processed by said main pumping means, by means of catalytic action and/or electrolysis, and pumping-processing oxygen produced by said decomposition; and
   said measurement gas component contained in said measurement gas is measured on the basis of a pumping current flowing through said measuring pumping means in accordance with said pumping process effected by said measuring pumping means.

3. The gas sensor according to claim 1, wherein:
   said electric signal-generating conversion means comprises an oxygen partial pressure-detecting means for decomposing said predetermined gas component contained in said measurement gas after being pumping-processed by said main pumping means, by means of catalytic action, and generating an electromotive force corresponding to a difference between an amount of oxygen contained in a reference gas and an amount of oxygen produced by said decomposition; and
   said measurement gas component contained in said measurement gas is measured on the basis of said electromotive force detected by said concentration-detecting means.

4. The gas sensor according to claim 1, wherein said oxygen concentration-detecting means comprises an auxiliary pumping means for pumping-processing oxygen contained in said measurement gas after being pumping-processed by said main pumping means, and a value of a pumping current flowing through said auxiliary pumping means is used as said detected value of oxygen concentration.

5. The gas sensor according to claim 1, wherein said oxygen concentration-detecting means comprises an oxygen partial pressure-detecting means for detecting a difference in partial pressure between oxygen contained in said measurement gas after being pumping-processed by said main pumping means and oxygen contained in a reference gas space, and a value of an electromotive force generated on the basis of said difference in partial pressure is used as said detected value of oxygen concentration.

6. The gas sensor according to claim 1, wherein said correcting control means comprises:
   a comparing means for determining a difference between said detected value supplied from said oxygen concentration-detecting means and said second reference value; and
   a reference value-correcting means for reflecting said difference supplied from said comparing means to said first reference value for said main pumping means.

7. The gas sensor according to claim 1, wherein said self-diagnosis means judges that any abnormal condition occurs, when said detected voltage or current value supplied from said oxygen concentration detecting means does not arrive at said prescribed range for a predetermined period of time.

8. The gas sensor according to claim 1, wherein said self-diagnosis means comprises:
   a comparing means for comparing said detected value supplied from said oxygen concentration-detecting means with said prescribed range; and
   a monitoring means for temporarily or periodically monitoring a comparison output supplied from said comparing means and judging that any abnormality occurs, when said comparison output does not arrive at said prescribed range for a predetermined period of time.

9. The gas sensor according to claim 8, wherein said monitoring means monitors said comparison output supplied from said comparing means at intervals of a certain period of time for said predetermined period of time.

10. The gas sensor according to claim 8, wherein said monitoring means monitors said comparison output supplied from said comparing means for said predetermined period of time, which period ends upon completion of a predetermined condition.

* * * * *